US008507017B2

(12) United States Patent
Wu

(10) Patent No.: US 8,507,017 B2
(45) Date of Patent: Aug. 13, 2013

(54) METHOD FOR DECREASING NICOTINE AND OTHER SUBSTANCE USE IN HUMANS

(75) Inventor: Jie Wu, Avondale, AZ (US)

(73) Assignee: Arizona Health Consulting Group, LLC, Chandler, AZ (US)

( * ) Notice: Subject to any disclaimer, the term of this patent is extended or adjusted under 35 U.S.C. 154(b) by 546 days.

(21) Appl. No.: 11/972,993

(22) Filed: Jan. 11, 2008

(65) Prior Publication Data

US 2008/0176887 A1 Jul. 24, 2008

Related U.S. Application Data

(63) Continuation of application No. 10/360,112, filed on Feb. 7, 2003, now Pat. No. 7,341,745.

(51) Int. Cl.
A61K 36/899 (2006.01)
A61K 36/00 (2006.01)
A61K 31/70 (2006.01)

(52) U.S. Cl.
USPC ........... 424/750; 424/725; 424/774; 424/779; 424/773; 514/43

(58) Field of Classification Search
None
See application file for complete search history.

(56) References Cited

U.S. PATENT DOCUMENTS

| | | | |
|---|---|---|---|
| 4,517,172 | A | 5/1985 | Southard |
| 4,590,061 | A | 5/1986 | Southard |
| 4,767,861 | A | 8/1988 | Boulware |
| 4,818,533 | A | 4/1989 | Boulware et al. |
| 5,242,926 | A | 9/1993 | Hsieh et al. |
| 5,308,619 | A | 5/1994 | Schneider et al. |
| 5,411,733 | A | 5/1995 | Hozumi et al. |
| 5,417,979 | A | 5/1995 | Fan et al. |
| 5,547,956 | A | 8/1996 | Qu et al. |
| 5,616,324 | A | 4/1997 | Foster et al. |
| 5,876,728 | A | 3/1999 | Kass et al. |
| 6,210,680 | B1 | 4/2001 | Jia et al. |
| 6,217,880 | B1 | 4/2001 | Lan |
| 6,239,139 | B1 | 5/2001 | Kim et al. |
| 6,255,317 | B1 | 7/2001 | Kim et al. |
| 6,933,291 | B2 | 8/2005 | Qi et al. |
| 7,341,745 | B2 * | 3/2008 | Wu .............................. 424/725 |
| 2001/0000731 | A1 | 5/2001 | Jia et al. |
| 2001/0038863 | A1 | 11/2001 | Jaenicke et al. |
| 2002/0031559 | A1 | 3/2002 | Liang et al. |
| 2002/0039587 | A1 | 4/2002 | Tao |
| 2002/0041906 | A1 | 4/2002 | Tao |
| 2002/0068097 | A1 | 6/2002 | Basu |

FOREIGN PATENT DOCUMENTS

| | | |
|---|---|---|
| JP | 01016722 | 1/1989 |
| JP | 2000256326 | 11/2000 |
| JP | 2000-191530 | 11/2002 |

OTHER PUBLICATIONS

Albuquerque (Physiol. Rev. (2009), vol. 89, pp. 73-120).*
Ge et al. (Yangzhou Daxue Xuebao Bianjibu (1998), vol. 1, No. 2, pp. 49-51).*
Wang et al. (Acta Pharmacologica Sinica (1982), vol. 3, No. 2, pp. 73-77).*
Schroeder et al. (Society for Neuroscience Abstract Viewer and Itinerary Planner (2002), vol. 2002, pp. Abstract No. 137.7; 32nd Annual Meeting of the Society for Neuroscience, Nov. 2002).*
Ge et al. Experimental Study of Petraphyhydroprotoberberines Inhibiting Morphine Withdrawal Syndrome. Zhongguo Yaowu Yilaixing Zazhi (1999), 8(3) Abstract.*
Blanchfield et al., "Alkaloids From Some Australian *Stephania* (*Menispermaceae*) Species," Natural Product Letters, 3 (4):305-312, 1993.
Dharmananda, S., "Alzheimer's Disease: Treatment with Chinese Herbs," Institute for Traditional Medicine, Portland, Oregon, 1996.
Iwasa et al., "Structure-activity relationships of protoberberines having antimicrobial activity," Planta Med, 64 (8):748-51, 1998, abstract only.
National Center for Complementary and Alternative Medicine (NCCAM), "A Ramdomized Controlled Trial of the Use of Craniosacral Osteophatic Manipulative Treatement and of Botanical Treatment in Recurrent Otitis Media in Children.", Jul. 29, 2002.

(Continued)

*Primary Examiner* — Chris R Tate
*Assistant Examiner* — Deborah Davis
(74) *Attorney, Agent, or Firm* — Robert D. Atkins; Patent Law Group: Atkins & Associates, P.C.

(57) ABSTRACT

A method for decreasing nicotine and other substance use in humans is disclosed. Tetrahydroberberine (THB) and its analogs, l-Tetrahydropalmatine (l-THP) and l-Stepholidine (l-SPD), are present in and can be isolated from several plants in the Magnoliidae superorder. According to the disclosed method, THB and its analogs are used to block nicotine-induced DA release, and modulate heterologous or homoeric expression of human nicotinic acetylcholine receptors (nAChR) in humans. Specifically, THB exhibits bi-directory modulation of $\alpha 4\beta 2$-nAChR-mediated currents induced by nicotine. THB also shows predominant inhibition on homologously expressed $\alpha 7$-nAChR function. Thus, according to the disclosed method, THB is used to simultaneous blockade midbrain DA system function, the brain reward center, and neuronal $\alpha 4\beta 2$- and $\alpha 7$-nAChR function, the major nicotine targets in the brain. Therefore, THB and its analogs serve as a novel class of natural compounds to decrease nicotine dependence in humans. Furthermore other substances, such as alcohol, cocaine, and opiates, also operate by triggering the brain reward center, resulting in a cycle of substance or alcohol abuse. THB and its analogs can be used to decrease use of substances such as alcohol, cocaine, and opiates. Finally, because THB and its analogs are DA antagonists, THB and its analogs can also be used as a treatment for Parkinson's Disease, Alzheimer's Disease and Schizophrenia.

29 Claims, 12 Drawing Sheets

(56) References Cited

OTHER PUBLICATIONS

Niwa et al., "Dopaminergic Unique Affinity of Tetrahydroberberine and I-Tetrahydroberberine-d-Camphor Sulfonate,", Pharmacology, 43:329-336, 1991.

Pan et al., "Improved Preparation of Tetrahydropalmatine from *Fibraurea tinctoria*," Pharmaceutical Industry, 19 (7):319-320, 1988.

Sheng et al., "Treatment of chloroquine-resistant malaria using pyrimethamine in combination with berberine, tetracycline or cotrimoxazole," East Afr Med Journal, 74(5):283-4, 1997, abstract only.

Vetulani, J., "Drug Addiction: Part III. Pharmacotherapy of Addiction," Polish Journal of Pharmacology, 53:415-434, 2001.

Wang et al., "Effect of tetrahydroberberine on blockade of preand postsynaptic dopamine receptors," Shanghai Institute of Materia Medica, Chinese Academy of Sciences, Shanghai, China, 3(2):73-77, 1982, abstract only Acta Pharmacolgica Sinica.

Wu et al., "Tetrahydroberberine suppresses dopamine-induced potassium current in acutely dissociated CA1 pyramidal neurons from rat hippocampus," Neuroscience Letters, 207:155-158, 1996.

Wu et al., "Tetrahydroberberine inhibits acetylcholine-induced K+ current in acutely dissociated rat hippocampal CA1 pyramidal neurons," Neuroscience Letters 222:115-118, 1997.

Wu et al., "Tetrahydroberberine blocks membrane K+ channels underlying its inhibition of intracellular message-mediated outward currents in acutely dissociated CA1 neurons from rat hippocampus,", Brain Research, 775:214-218, 1997.

Zhang et al., "Comparison of (−)-stepholidine and D1 or D2 agonists on unit firing of globus pallidus in 6-hydroxydopamine-lesioned rats," Life Sciences, 63(7):637-544, 1998.

http://www.netdoctor.co.uk/diseases/facts/stroke.htm—accessed Jan. 2008.

http://www.merriam-webster.com/dictionary/ischemia—accessed Jan. 2008.

Shen et al., "Protective Effect of 1-stepholidine on Cerebral Ischemia-reperfusion Damage in Rats," Chinese Journal of Pharmacology and Toxicology, 2001, vol. 15, No. 5, pp. 395-397.

Liang et al, "Protective Effects of D1-Tetrahydropalmatine on Focal Brain Ischemia—Reperfusion Injury in Rats," Chinese Pharmacology Bulletin, 1998, vol. 14, No. 5, pp. 413-414.

Zhu et al., "Electrophysiological Study on Biphasic Firing Activity Elicited by D1 Agonistic D2 Antagonistic Action of—stepholidine in Nucleus Accumbens," Acta Physiologica Sinica, 2000, vol. 52, No. 3, pp. 123-130.

Jin et al., "-Stepholidine: A Potential Novel Antipsychotic Druge with Dual D1 receptor Agonist and D2 Receptor Antagonist Actions," Trends in Pharmacological Sciences, Jan. 2002, vol. 23, No. 1, pp. 4-7.

Chang et al., "The Neuroprotective Effect of DL-Tetrahydropalmatine in Rat Heatstroke ," Neuroscience Letter, 1999, vol. 267, pp. 109-112.

\* cited by examiner

A

B

METHOD FOR DECREASING NICOTINE AND OTHER SUBSTANCE USE IN HUMANS

CLAIM OF DOMESTIC PRIORITY

The present application is a continuation of U.S. application Ser. No. 10/360,112, now U.S. Pat. No. 7,341,745, filed on Feb. 7, 2003, entitled "Method for Decreasing Nicotine and other Substance Use in Humans," and claims priority to the foregoing parent application pursuant to 35 U.S.C. §120.

CROSS-REFERENCE TO RELATED APPLICATIONS

The present patent application is related to co-pending U.S. divisional patent application Ser. No. 12/013,089, filed on Jan. 11, 2008. The present patent application is further related to co-pending U.S. divisional patent application Ser. No. 12/013,224, filed Jan. 11, 2008.

FIELD OF THE INVENTION

The present invention relates generally to a method for decreasing human's cravings for cigarettes and reducing instances of relapse during detoxification once smoking abstinence has been achieved, and more specifically, to a method for decreasing nicotine use by treating a human with a novel class of natural compounds such as tetrahydroberberine (THB) and its analogs, isolated from the Magnoliidae superorder of plants, such as *Corydalis* and *Stephania*.

BACKGROUND OF THE INVENTION

Cigarette smoking is a prevalent, modifiable risk factor for increased morbidity and mortality in the United States, and perhaps in the world. Smokers incur medical risks attributable to direct inhalation. Bystanders, termed passive smokers, also incur medical risks from second-hand smoke. Society, as a whole, also bears the economic costs associated with death and disease attributable to smoking. Although the majority of smokers have tried repeatedly to quit smoking, eighty percent of smokers return to tobacco in less than two years after quitting. Therefore, tobacco dependence is a health hazard for millions of Americans.

Nicotine is the principal alkaloid in tobacco and is primarily responsible for tobacco dependence. The initiation and maintenance of tobacco dependence in a human is due to certain bio-behavioral and neuromolecular mechanisms. Nicotinic acetylcholine receptors (nAChRs) in humans are the initial binding sites for nicotine. The binding of nicotine to nAChRs modulates the brain's "reward" function by triggering dopamine release in the human brain.

Although a variety of psychopharmacological effects contribute to the reinforcing action, the existence of a mesolimbic dopaminergic pathway for nicotinic reward is the predominant hypothesis. The mesolimbic dopaminergic pathway originates in the ventral tegmental area (VTA) of the midbrain and projects to forebrain structures including the prefrontal cortex and to limbic areas such as the olfactory tubercle, the amygdala, the septal region, and the nucleus accumbens. Many studies have indicated that dopamine release in the nucleus accumbens of the human brain is "rewarding" or signals an encounter with a "reward" from the environment. Other substances, such as alcohol, cocaine, and opiates, operate in the same manner, resulting in a cycle of substance or alcohol abuse.

Therefore, a need exists for a novel compound that can block the dopamine release system to abolish nicotinic stimulation or smoking-induced "rewarding" and/or can block nAChRs to limit increasing nicotine-induced dopamine release.

SUMMARY OF THE INVENTION

The present invention provides a method for decreasing nicotine use in living organisms, for example, in humans. In one embodiment, and by way of example only, the method includes administering a dose of Magnoliidae to the living organism providing at least one Magnoliidae compound, selected from the group Tetrahydraberberine (THB), Tetrahydropalmatine (l-THP) and Stepholidine (l-SPD), in an effective amount to reduce nicotine use by the living organism. The dose of Magnoliidae can be administered, for example, orally, sublingually, dermally, subcutaneously, intravenously or through respiratory inhalation.

In another exemplary embodiment, a method for reducing sensitization to nicotine in a living organism includes administering a dose of THB, l-THP, l-SPD, or analogs of THB, following extraction from one or more Magnoliidae plants. In one embodiment, and by way of example only, THB analogs include a conserved four-ring structure, that in another example, include a benzene-hexane-hexane-benzene structure.

Other independent features and advantages of the method for decreasing nicotine use in living organisms will become apparent from the following detailed description, taken in conjunction with the accompanying drawings which illustrate, by way of example, the principles of the invention.

DETAILED DESCRIPTION OF VARIOUS EMBODIMENTS

This description discloses a method for reducing smoking in humans by treating a human with one of a group of chemical analogs isolated from select genera of the Magnoliidae superorder of plants.

Figure 1:
FIG. 1 is an illustration of a *Corydalis ambigua* plant.

FIG. 1 is an illustration of one species of *Corydalis*, specifically, *Corydalis ambigua* 10. *Corydalis ambigua* 10 is one species of the *Corydalis* genus of herbal plants, primarily found in East Asia, namely China, and Japan. Mature *Corydalis ambigua* 10 is about 150.0 cm in height and about 80.0 cm in width. *Corydalis ambigua* 10 is a perennial herb. *Corydalis* is a genus of the Fumariaceae sub-family, the Papoveraceae family, the Papaverales order and the Magnoliidae superorder of plants.

Figure 2:
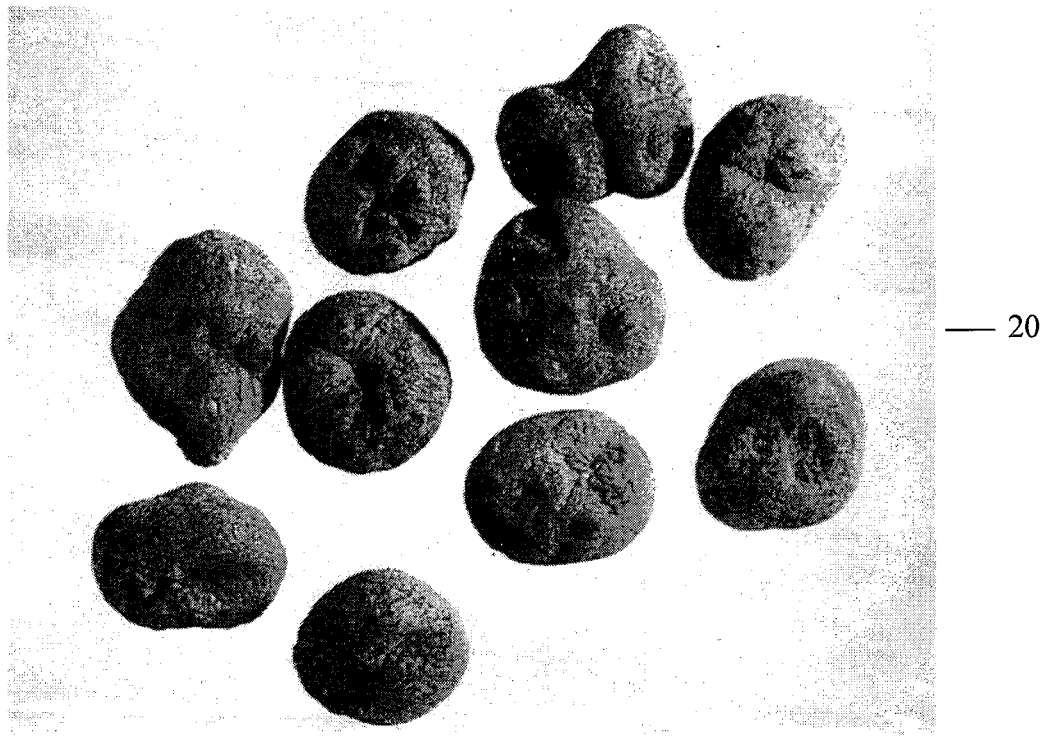
FIG. 2 is an illustration of tubers from the *Corydalis ambigua* plant.

FIG. 2 is a depiction of the tubers 20 of the *Corydalis ambigua* plant. While one embodiment specifically refers to using the *ambigua* species, any species of *Corydalis* containing tetrahydroberberine (THB) or its analogs may be used. Thus, the term *Corydalis* refers to all species of *Corydalis* containing THB or its analogs, including *Corydalis ambigua*. Although, one embodiment specifically envisions extracting THB and its analogs from the tubers 20 of the *Corydalis ambigua*, THB and its analogs can be extracted by purifying any of the plant parts, including, but not limited to, the leaves, stem, and tubers. Furthermore, a second embodiment envisions administering *Corydalis*, without prior purification of THB or its analogs. Thus, the term *Corydalis* encompasses the entire *Corydalis* plant and also all extracts derived from the *Corydalis* plant.

Figure 3:
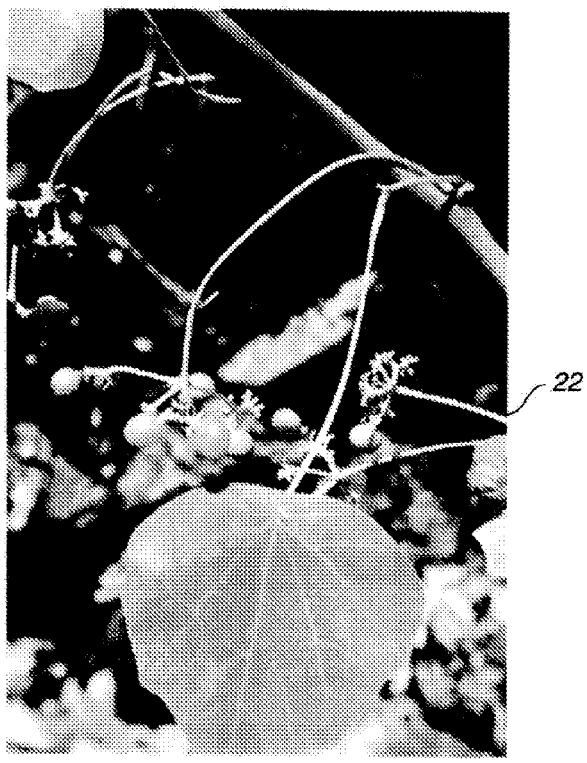
FIGS. 3A-3B are illustrations of a *Stephania* plant and tubers from the *Stephania* plant.
Figure 3:
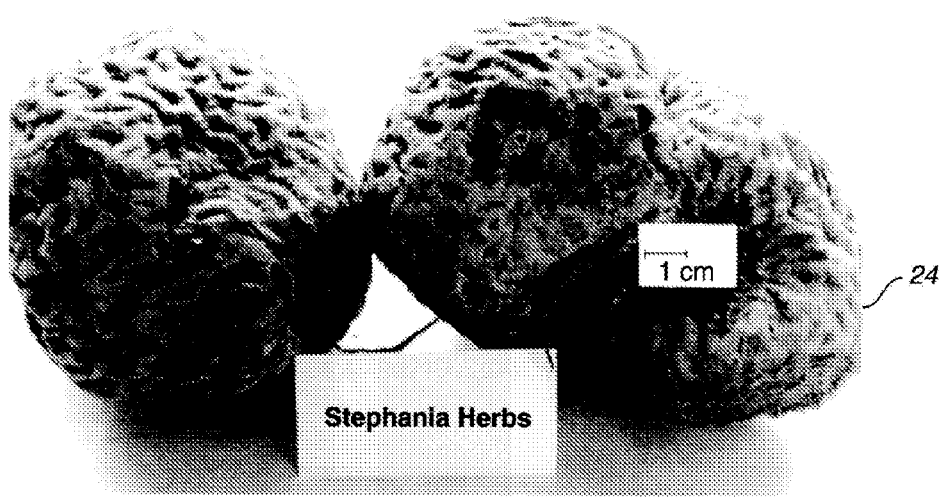

FIG. 3A is an illustration of one species of the *Stephania* genus of plants, also a genus of herbal plants, primarily found in East Asia. FIG. 3B is a depiction of the tubers of the *Stephania* plant. The *Stephania* genus of plants includes, but is not limited to, *Stephania intermedia, Stephania hainanensis*, and *Stephania yunnanensis*. The *Stephania* genus of plants contains analogs of THB. Specifically, *Stephania intermedia, hainanensis*, and *yunnanensis* contain l-tetrahydropalmatine (l-THP or dl-THP) while both *Stephania intermedia* and *yunnanensis* contain l-Stepholidine (l-SPD). L-THP can also be found in and purified from *Fibraurea recisa* Pierre. Both *Stephania* and *Fibraurea* are from the Menispermaceae family and the Ranunculales order of plants. As with *Corydalis*, both *Stephania* and *Fibraurea* belong to the Magnoliidae superorder of plants.

As with *Corydalis*, one embodiment specifically envisions extracting l-THP and l-SPD from the tubers of the *Fibraurea* or *Stephania* plants. However, in a second embodiment, l-THP and l-SPD can be extracted by purifying any of the plant parts, including, but not limited to, the leaves, stem, and tubers. Yet another embodiment envisions administering any species of *Stephania* or *Fibraurea* without prior purification of l-THP or l-SPD.

Figure 4A:
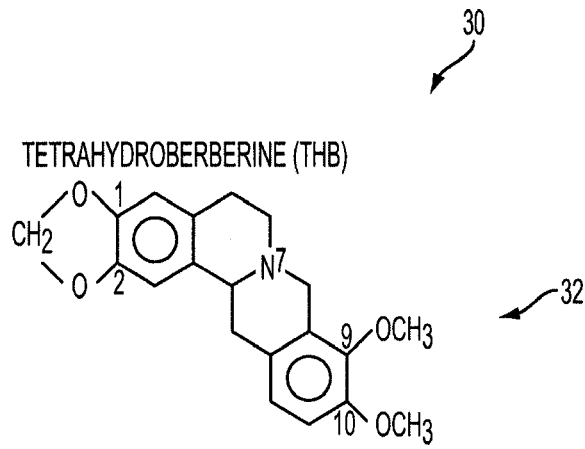
FIGS. 4A-4C show the chemical structure of Tetrahydroberberine (THB) and two analogs of Tetrahydroberberine (THB analogs)
Figure 4B:
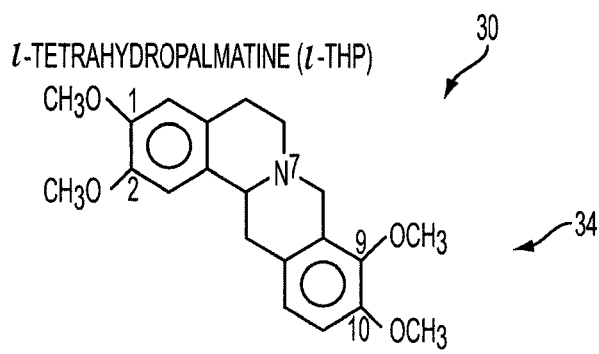
Figure 4C:
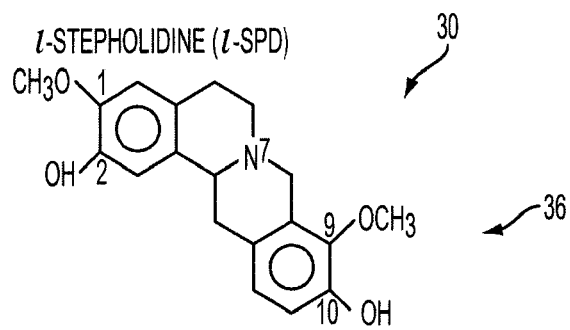

According to the present disclosure, the term Magnoliidae will be used to refer to all species in the Magnoliidae superorder of plants that contain THB, l-THP, l-SPD, or any analog of THB, l-THP, or l-SPD. FIGS. 4A-C show the chemical structure of compounds 30 isolated from Magnoliidae plants. According to one embodiment, compounds 30 can be referred to collectively as "Magnoliidae compounds" or each, singularly, as "a Magnoliidae compound." However, according to one embodiment, Magnoliidae compounds are not limited to the Magnoliidae compounds 30 shown, but also include any analog of Magnoliidae compounds 30. In one embodiment, analog of Magnoliidae compounds 30 can be characterized by a conserved four-ring structure. For example, the analogs can have a conserved benzene-hexane-hexane-benzene structure, as shown in all Magnoliidae compounds 30.

FIG. 4A shows the chemical structure of Tetrahydroberberine (THB) 32. FIG. 4B shows the chemical structure of one analog of THB 32, l-Tetrahydropalmatine (l-THP) 34. FIG. 4C shows the chemical structure of a second analog of THB 32, l-Stepholidine (l-SPD) 36. l-THP 34 and l-SPD 36 are homologue analogs of THB and are collectively referred to as THB analogs. Magnoliidae compounds 30 are extracted from one or more parts of any Magnoliidae species by Classical Alkaloid Chemical Purifying Method. In one embodiment, the Magnoliidae plant is immersed into an alkaline solution, extracted using benzene, then crystallized and purified to get THB 32, l-THP 34, and l-SPD 36. In another embodiment, if Magnoliidae compounds are not practically available as found in or extracted from Magnoliidae plants, Magnoliidae compounds may be synthesized or derived from other sources.

Magnoliidae compounds exhibit a marked depression effect in the central nervous system such as sedation, hypnosis and analgesia. The pharmacological mechanism of THB and its analogs involve working as a class of antagonists to inhibit brain dopamine receptor (DA) function, blockade of α-adrenergic receptor and 5-TH receptor functions, and direct modulation of ion channel function.

Numerous biochemical and behavioral experiments have indicated that THB and its analogs exhibit all the characteristics of a DA antagonist. Compared with traditional DA receptor antagonists, the Magnoliidae compounds exhibit two unique properties. First, THB possesses an equipotent effect on D1-type and D2-type DA receptor binding. Second, in normal rats, l-SPD exhibits the characteristics of D2 receptor antagonist, while in rats with unilateral nigral lesion (DA receptor super sensitivity in striatum), l-SPD acts on D1 receptors as an agonist. Therefore, by blocking DA receptor function, Magnoliidae compounds block nicotine-induced DA release, which is the major cellular mechanism of nicotine reward and dependence.

Basic cellular mechanisms of nicotinic dependence also involve the functional state changes during repeated nicotinic agonists exposure and receptor changes in the number of receptors during chronic nicotinic exposure. Nicotinic Acetylcholine Receptors (nAChRs) can exist in many different functional states, such as resting, activation, desensitization or inactivation. The desensitization of nAChRs plays an important role in initiating nicotinic tolerance and dependence. Recovery from receptor desensitization contributes to nicotinic withdrawal symptoms.

Magnoliidae compounds possess clear modulating effects on heterologous expression of human nicotinic acetylcholine receptors (nAChRs) in the native nAChR-null SH-EP1 human epithelial cell line using patch-clamp techniques. nAChRs are prototypical members of the ligand-gated ion channel superfamily of neurotransmitter receptors. nAChRs provide both classical and contemporary models for the establishment of concepts pertaining to mechanisms of drug action, synaptic transmission, and structure and function of transmembrane signaling compounds.

The nAChRs that mediate depolarizing inward sodium ($Na^+$) current play important roles in classical excitatory neurotransmission at the nerve-muscle junction, through autonomic ganglia, and perhaps in a variety of central nervous system cholinergic pathways that contribute to processes such as perception, cognition, and emotion. nAChRs on nerve terminals also exist on motor, preganglionic and central neurons, and these nAChRs can regulate release of acetylcholine (ACh) or other neurotransmitters, meaning that some nAChRs also modulate neurotransmissions.

nAChRs exist as a diverse family of proteins composed of different combinations of subunits derived from at least seventeen different genes ($α1$-$α10$, $β1$-$β4$, $γ$, $δ$, and $ε$). Naturally expressed nAChRs in muscle are made from $α1$, $β1$ $δ$ and either $γ$ (in fetal tissue) or $ε$ (in adult tissue) subunits and have properties just like those of heterologously expressed nAChR made of the same subunits. nAChR can form as homomers of the most ancient subunits, $α7$, $α8$, $α9$ or $α10$, although $α7$ plus α8, α9 plus α10, and other higher order complexes can also form in heterologous expression systems or can also form naturally.

Binary complexes of α2, α3 α4 or α6 subunits with β2 or β4 subunits also can form distinctive nAChR subtypes, at least in heterologous expression systems. α5 and β3 subunits are likely "wild-cards" able to integrate into at least some of the α/β binary complexes to form ternary complexes with unique properties, and more than one kind of a or β subunit can exist in some nAChR subtypes, for example, naturally expressed α3α5β2β4-nAChRs in postganglionic neurons and α4α6β2-nAChR in heterologous expression systems. Therefore, in one embodiment, heterologous, de novo expression of functional, α4β2-nAChR in a cloned epithelial cell line was used to demonstrate the efficacy of Magnoliidae compounds.

Figure 5:
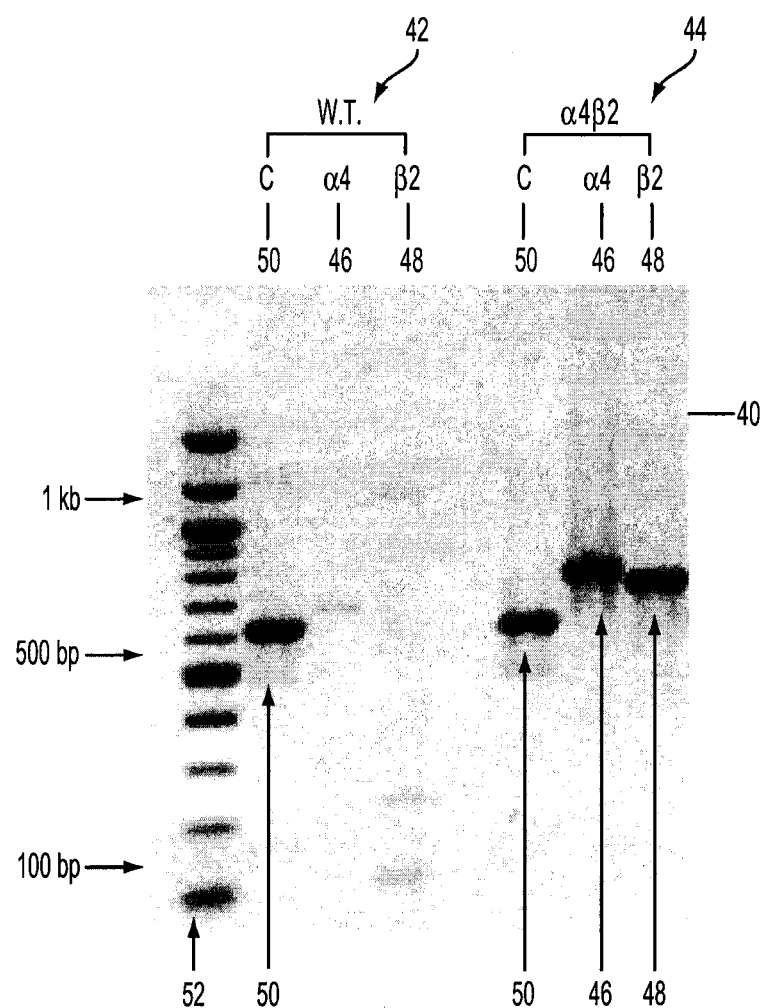
FIG. 5 illustrates the detection of $\alpha 4$ and $\beta 2$ nAChR subunit transcripts by RT-PCR in wild-type SH-EP1 cells and cells co-transfected with $\alpha 4$ and $\beta 2$ cDNA.

FIG. 5 depicts the detection of α4 and β2 nAchR subunit transcripts by reverse transcription polymerase chain reaction RT-PCR in wild-type (WT) human SH-EP1 (nAchR-null human epithelial) cells 42 and human SH-EP1 cells co-transfected with α4 and β2 cDNA 44 on an agarose gel 40. In FIG. 4, cDNA was synthesized from 0.8 microgram (μg) of total RNA prepared from wild type SH-EP1, SH-EP1-α4β2, and SH-EP1 α4β4 cells using oligo d(T)$_{12-18}$ primer in a RT reaction. One-tenth of the RT product was then used in each PCR with gene-specific primers for α4 46, β2 48, or GAPDH (lanes C as internal control) 50. One-tenth of each 50 μl RT-PCR product was then resolved on one percent agarose gel. The 100 base pair DNA ladder 52 was used as the molecular weight marker. The presence of α4 46 and β2 48 subunits are seen in the co-transfected cells 44, whereas both are absent in the WT cells 42. Thus, RT-PCR confirms the expression of α4 and β2 nAChR subunits.

In FIGS. 6-9, whole-cell patch-clamp recording techniques in voltage-clamp mode were used to detect changes in current. Conventional whole-cell current recording coupled with techniques for fast application and removal of agonist (9 channel multi-barrel pipette), were applied in this study. Briefly, cells plated on poly-lysine-coated 35-mm culture dishes were placed on the stage of an inverted microscope (Olympus iX7, Lake Success, N.Y.) and continuously superfused with standard external solution (2 ml/min). Glass microelectrodes (3-5 MΩ resistance between pipette and extracellular solutions) were used to form tight seals (>1 GΩ) on the cell surface until suction was applied to convert to conventional whole-cell recording.

Cells were then voltage-clamped at holding potentials of −60 mV and ion currents in response to application of ligands were measured (Axon Instruments 200B amplifier, Foster City, Calif.), typically using data filtered at 2 kHz, acquired at 5 kHz, displayed and digitized on-line (Axon Instruments Digidata 1200 series A/D board), and stored to computer hard drive. Both pipette and whole current capacitance were minimized and the series resistance was routinely compensated to 80%. The access resistance before series resistance compensation was between 10-20 MΩ. Data acquisition and analyses were done using Pclamp8 (Axon Instruments), and results were plotted using Origin 5.0 (Microcal, North Hampton, Mass.).

Data usually were fit over the 10-90% period from inward current peak until agonist exposure was terminated (5-10 sec). The experimental data are presented as means±standard errors, and comparisons of different conditions were analyzed for statistical significance using the Student's t-tests. All experiments were performed at room temperature (22±1° C.). A pipette electrode solution comprising TrisPO$_4$dibasic 110 milli-Molar (mM), Trisbase 28 mM, Ethylenediamine-tetraacetate (EDTA) 11 mM, Magnesium Chloride (MgCl$_2$) 2 mM, Calcium Chloride (CaCl$_2$) 0.5 mM, and Sodium-Adenosine Triphosphate (Na-ATP) 4 mM, resulting in a pH of 7.3, was used.

Figures 1, 6A:
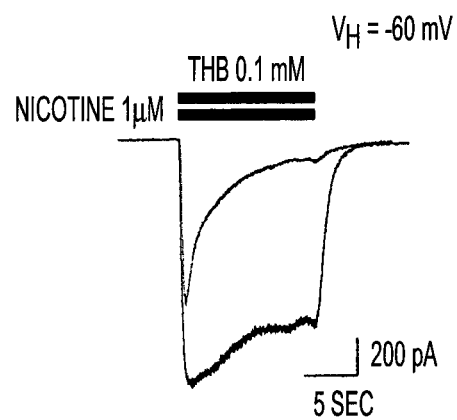
FIGS. 6A-6B are a series of graphs illustrating effects of THB and THB analogs on $\alpha 4\beta 2$-nAChR responses and the effects of THB on nicotinic responses mediated by different nAChR subtypes.
Figures 2, 6A:
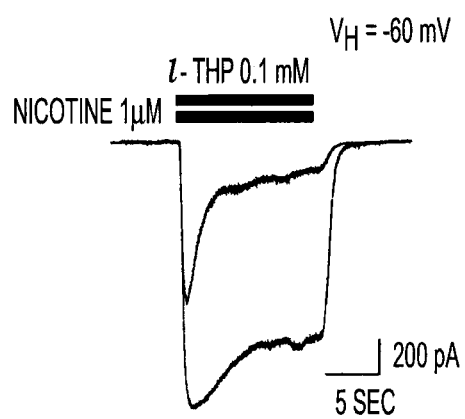
Figures 3, 6A:
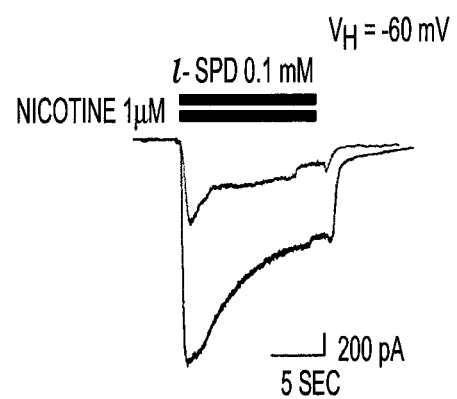

FIG. 6A illustrates the effects of high concentrations of Magnoliidae compounds on α4β2-nAChR responses. The series of graphs illustrate the similar effects of THB (1), l-THP (2) and l-SPD (3), respectively on α2β4-nAChR mediated currents. A concentration of 0.1 mM of each Magnoliidae compound was used. The results demonstrate that each of the Magnoliidae compounds exhibits clear pharmacological effects on human neuronal nAChRs expressed in the human epithelia cell-line. The major pharmacological effect of Magnoliidae compounds at high concentrations is inhibition of nAChR function. In FIG. 6A, the inhibition of nAChR function is represented by the reduction of peak current response and the acceleration of the steady-state component.

Figures 1, 6B:
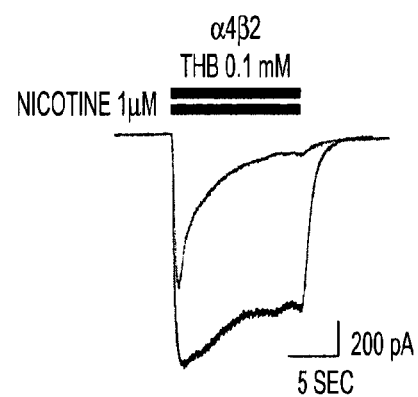
Figures 2, 6B:
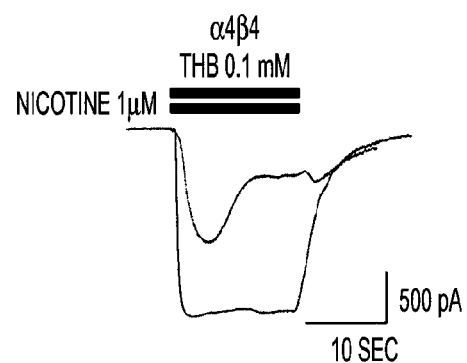
Figures 3, 6B:
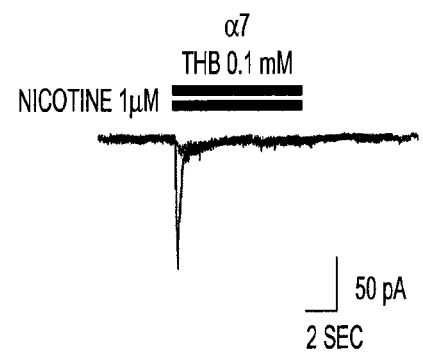

In FIG. 6B, the effects of Magnoliidae compounds on nicotinic responses mediated by different nAChR subtypes are shown. In FIG. 6B, the effects of Magnoliidae compounds on α4β2 (1), α4α4 (2) and α7 (3) subtypes is shown. In FIG. 6B, THB, at a concentration of 0.1 mM, was used as the representative Magnoliidae compound. Nicotine, at a concentration of 1.0 μM, was again used as the control. In FIG. 6B, the inhibition of each nAChR subtype function is represented by the reduction of peak current response and the acceleration of the steady-state component. As illustrated in graph (s), the inhibitory effect occurs more predominantly in α7-nAChRs.

Figure 7A:
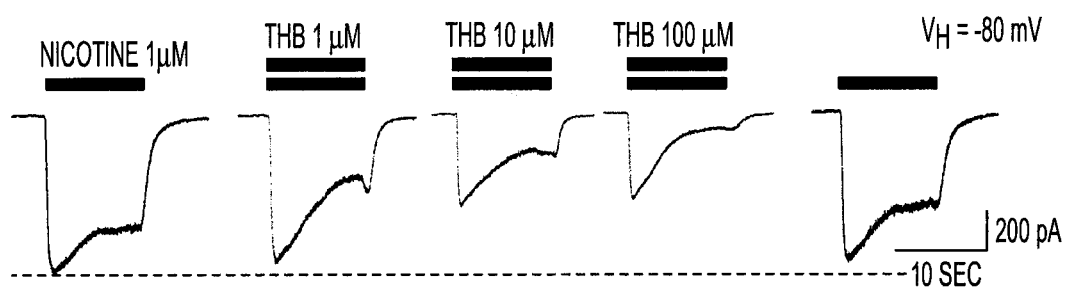
FIGS. 7A-7C are a series of graphs illustrating the effects of THB on nicotinic response.

FIG. 7A illustrates the concentration-dependent manner in which Magnoliidae compounds effect a nicotinic response in nAChRs. Graphs (1) and (5) illustrate nicotine-induced currents alone, at a concentration of 1.0 μM. Graphs (2), (3), and (4) illustrate the mediating effects of THB when added in the presence of nicotine, as the concentration of THB increases from 1.0 μM (2), to 10 μM (3) to 100 μM (4).

Figure 7B:
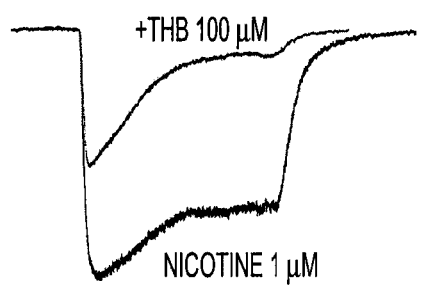
Figure 7C:
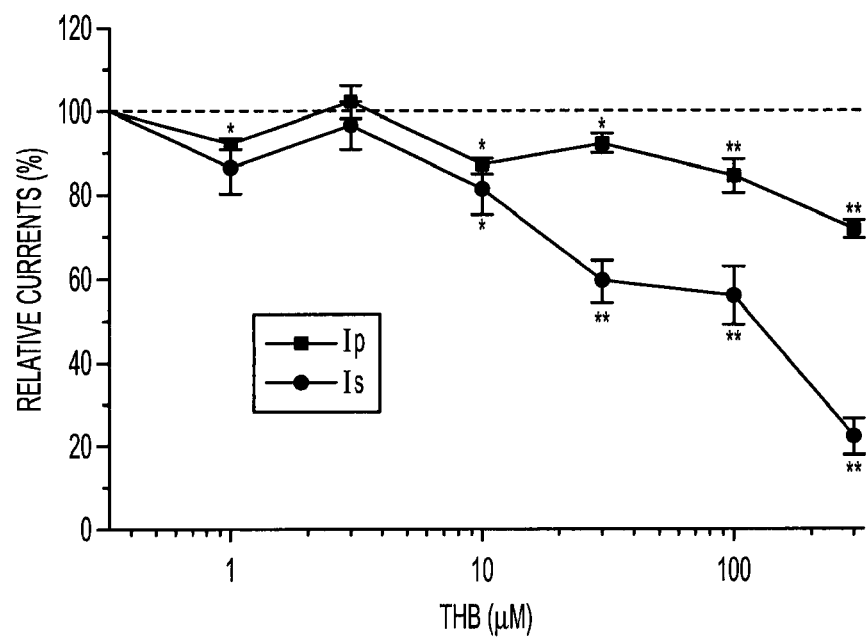

FIG. 7B further illustrates the difference in nicotine-induced currents between nicotine alone and the addition of 100 μM THB. Again, the inhibition of nAChR function is demonstrated by the reduction of peak current response and the acceleration of the steady-state component. FIG. 7C further illustrates this concentration-dependent inhibition as a graphical comparison of peak (Ip) and steady-state (Is) components of nicotinic responses at different THB concentrations.

Figure 8A:
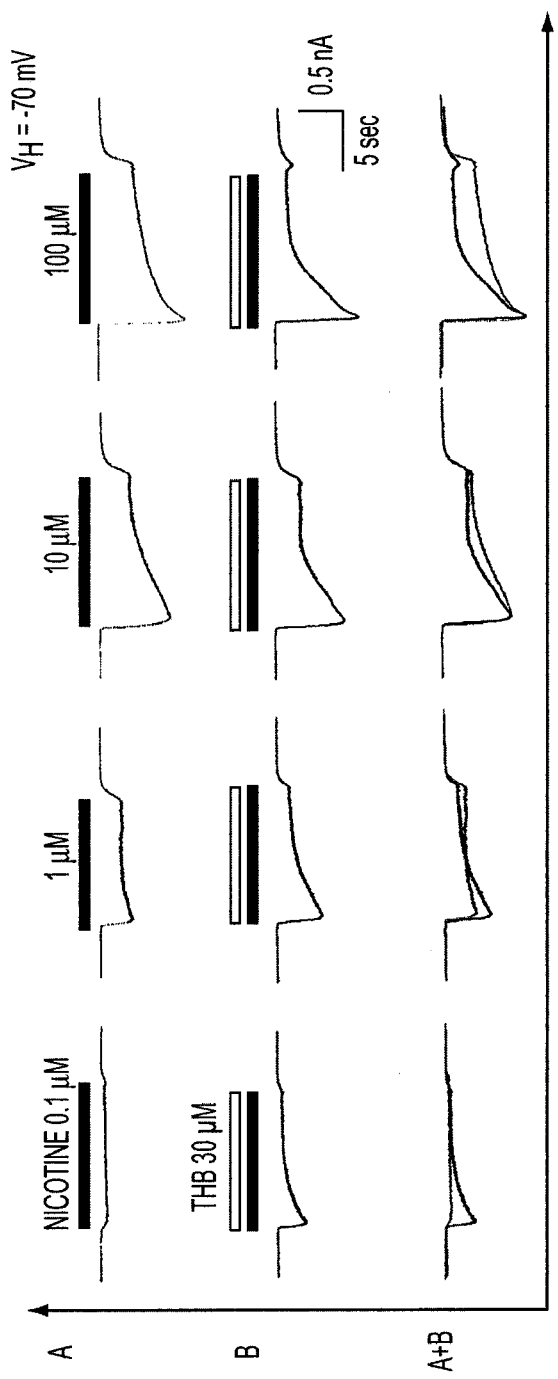
FIGS. 8A-8C further illustrate the effects of THB on nicotine responses.
Figure 8B:
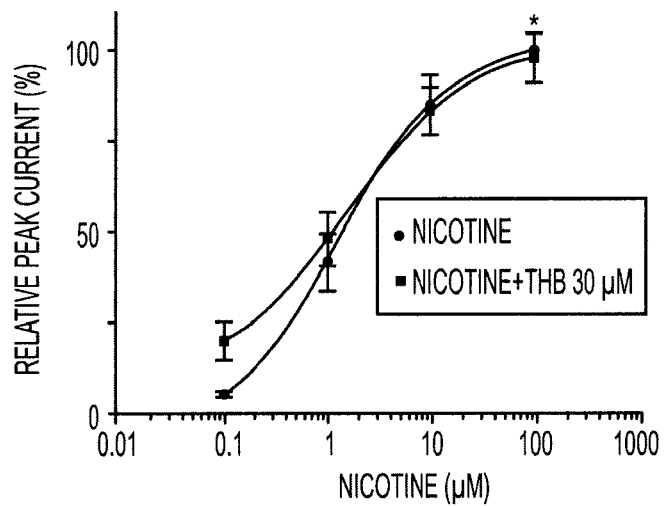

FIG. 8A illustrates nicotine-induced responses at different nicotine concentrations: 0.1 μM (1), 1.0 μM (2), 10 μM (3), and 100 μM (4). Low nicotine concentrations are representative of the concentration range in the brain of about 100-300 nano-Molar (mM) or 0.1-0.3 μM after one cigarette smoke. FIG. 8B illustrates the effects of THB at a concentration of 30 μM. In FIG. 8A+B, the superimposed graphs of FIGS. 8A and 8B demonstrate the ability of Magnoliidae compounds to modulate α4β2-nAChR function.

Figure 8C:
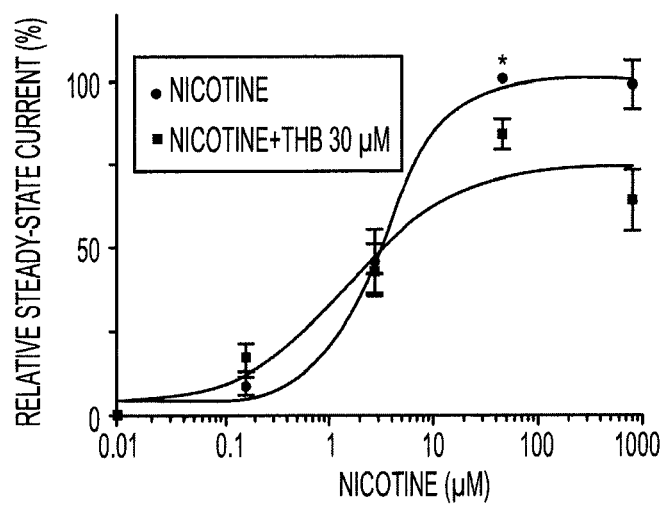

FIG. 8C shows the dose-response curves of nicotine-induce peak currents with and without THB, while FIG. 8D shows the dose-response curves of nicotine-induced steady-state currents with and without THB.

Figure 9A:
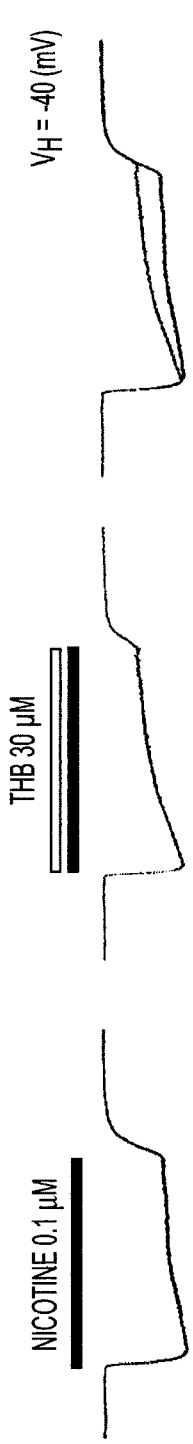
FIGS. 9A-9D illustrate how THB accelerates acute desensitization of nicotinic current.
Figure 9B:
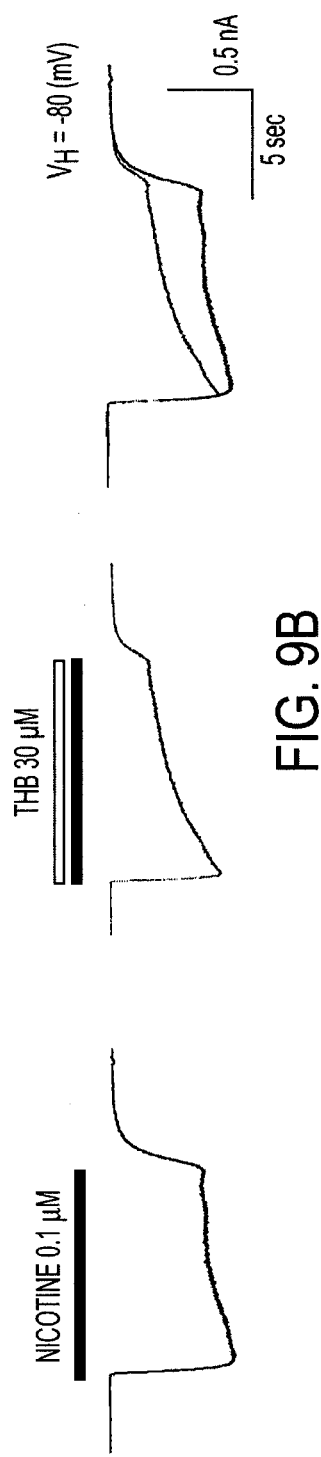
Figure 9C:
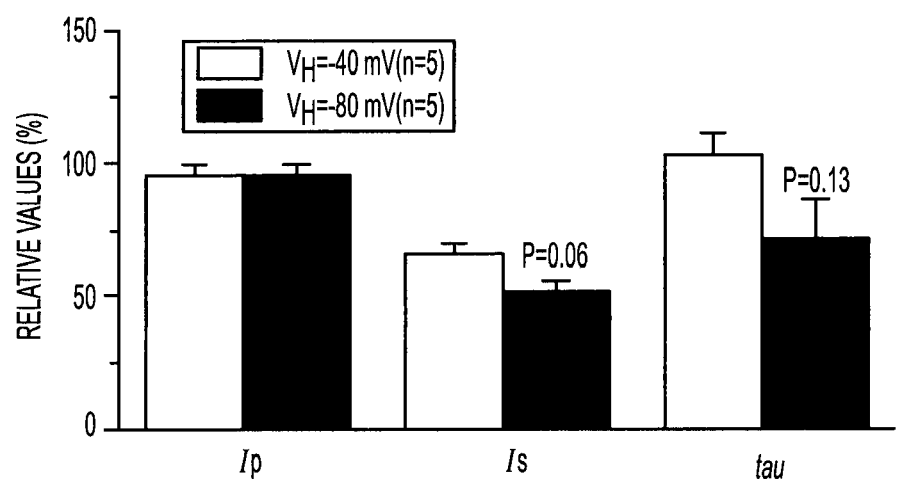
Figure 9D:
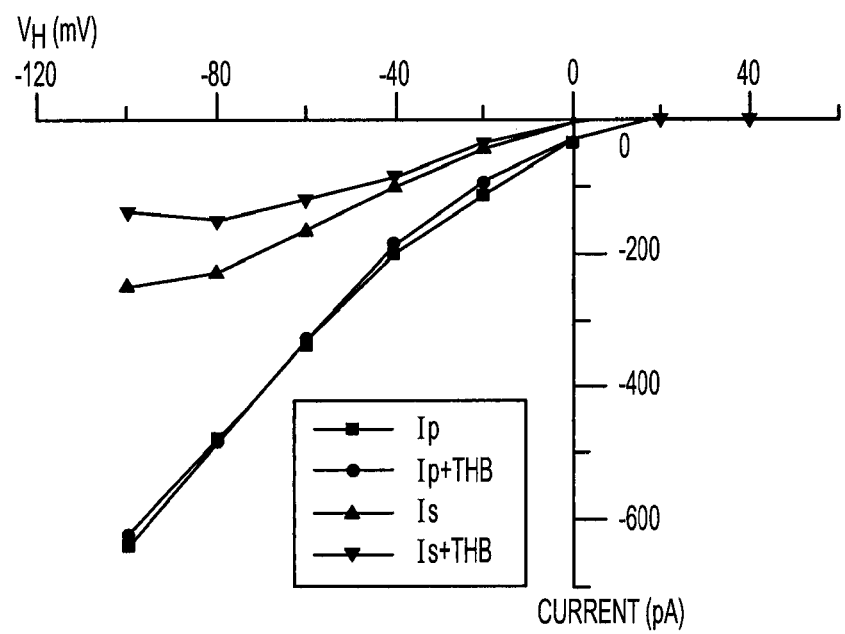

FIG. 9A and FIG. 9B demonstrate how THB, at a 30 μM concentration, accelerates acute desensitization of nicotine-induced currents at different holding potentials. In FIG. 9A, current-mediation is shown at a holding potential ($V_H$) of −40 milli-Volts (mV). In FIG. 9B, the accelerated acute desensitization is shown t a $V_H$ of −80 mV. The bar graph in FIG. 9C compares the relative values for the peak current (Ip), steady state (Is) and decay constant (tau) at two different voltages measured in FIGS. 9A and 9B. Finally, FIG. 9D compares the voltage dependent peak currents without THB (Ip) and in the presence of THB (Ip+THB). FIG. 9D also compares the voltage-dependent steady state currents without THB (Is) and in the presence of THB (Is+THB).

Through the mechanisms described above, Magnoliidae compounds serve to reduce nicotine use and produce smoking cessation in humans through one or more biological mechanisms. First, Magnoliidae compounds act as a DA receptor antagonist, reducing the reward processes in the brain produced by nicotine use. Second, Magnoliidae compounds cause nAChR modulation through bi-directory regulation of nAChR function, specifically through α4β2-nAChR-mediated currents induced by nicotine. At high agonist concentrations, Magnoliidae compounds diminish or even eliminate nAChR function by accelerating nAChR acute desensitization.

At low agonist concentrations, Magnoliidae compounds potentiate nicotinic response or enhance nAChR function. This potentiation may have increased efficacy when combining the Magnoliidae compound with nicotine-replacement therapy (NRT). If Magnoliidae compounds are used together with nicotine (either while still smoking or in conjunction with a nicotine additive or other nicotine-replacement therapy), the Magnoliidae compounds will block the brain reward center function (as the DA receptor antagonists) and reduce the reinforcement feeling, then gradually decrease the human's nicotine-dependence.

$^3$-H nicotine binding experiments demonstrate that Magnoliidae compounds exhibit a low affinity binding ability to α4αβ2-nAChR. At high concentrations, Magnoliidae compounds show more predominant inhibition on heterologously expressed α7-nAChR function. The ability to reduce nicotine use is further illustrated by the ability of Magnoliidae compounds to act on α4β2-nAChR subunits, α4β4-nAChR subunits, and α7-nAChR subunits.

Further, Magnoliidae compounds may act on α4β2-nAChR subunits combining with any other α or β subunit, including but not limited to α2, α3, α5, α6, or β3. Therefore, the simultaneous blockade of midbrain DA system function (the brain reward center) and neuronal α4β2-nAChR and α7-nAChR function (the major nicotine targets in the brain) by the Magnoliidae compounds, demonstrate that Magnoliidae compounds serve as a novel class of natural compounds for reducing nicotine use and producing smoking cessation in living organisms, particularly in humans.

The nAChRs densensitization, adaptation and up-regulation are the major cellular mechanism of nicotine tolerance, dependence and withdrawal. The major reason to fail in smoking cessation (quitting smoking) is the on-set of nicotine withdrawal symptoms. The basic cellular mechanism for withdrawal symptoms is that the numbers of nAChRs increase in the brain after long term exposure to nicotine. Once a human quits smoking, numerous nAChRs located on brain regions outside of the reward center will activate by an endogenous nicotinic receptor agonist, acetylcholine, and produce a series cardiac, respiratory and endo-secretary responses, called withdrawal symptoms.

Administration of Magnoliidae compounds will eliminate withdrawal symptoms by two mechanisms. First, the Magnoliidae compounds, at low nicotinic concentrations (<500 nM), enhance nAChR efficacy, thus decreasing the required nicotinic concentrations in the brain. Second, the Magnoliidae compounds, at slightly higher nicotinic concentrations (>1.0 μM), diminish nAChR function by acceleration of nAChRs desensitization. Therefore, the optimal way to achieve smoking cessation is to block the brain reward center (DA system) and block the over-expressed nAChR function. Magnoliidae compounds serve both functions and present a novel method to meet these needs, reducing nicotine use and sustaining smoking cessation.

The ability of Magnoliidae compounds to decrease nicotine use is further enhanced by the compounds' ability to act on no-epinephrine, epinephrine, and/or serotonin (5-TH) receptors. Because of the ability of Magnoliidae compounds to act on these receptors as well as acting as a DA receptor antagonist, reducing the reward processes in the brain, Magnoliidae compounds are also useful in treating other substance use, abuse and addiction. Therefore, Magnoliidae compounds can be administered to humans to reduce use of addictive substances, including reducing alcohol, cocaine, and opiate (or opioid) use.

Magnoliidae compounds also act on ion channels, such as calcium ($Ca^{2+}$) channels, potassium ($K^+$) channels, sodium ($Na^{2+}$) channels, or chloride ($Cl^-$) channels. For instance, FIG. 8 shows that Magnoliidae compound (THB) suppressed nicotinic response depending on $V_H$, meaning that THB may insert into nicotinic channel pores during nAChR activation to block these channels, termed 'open channel block' mechanism. 'Open channel block' may accelerate nAChR desensitization. The direct action of Magnoliidae compounds on $Ca^{2+}$ and $K^+$ channels, for example, also protects cardiac tissues and brain tissues against ischemia-induced injury.

Because of the manner in which Magnoliidae compounds act on biological mechanisms in the brain, as described above, Magnoliidae compounds can also be used in some neurological and psychological disorder treatment and prevention, for example, Alzheimer's Disease (AD) and Parkinson's Disease (PD). Specifically, co-administration of Magnoliidae compounds with levadopa (L-DOPA), as PD therapy, will prevent or significantly delay L-DOPA-induced akinesia. Furthermore, with the recent development of nicotinic agonists as a novel therapeutic strategy for both AD and PD, co-application of Magnoliidae compounds with low concentrations of the nicotinic agonists will increase efficacy and reduce the current side-effects that include nicotine tolerance and nicotine dependence. Finally, since midbrain DA receptor over-activity is the major cause of schizophrenia, the ability of Magnoliidae compounds to act as a DA receptor antagonist demonstrates that Magnoliidae compounds can be useful as an anti-schizophrenia agent.

According to clinical trial data, the optimal dosage to decrease nicotine use and produce smoking cessation is by administering a dose of 10-50 mg/Kg of body weight of one or more Magnoliidae compounds, including THB, 1-THP, 1-SPD, or any other THB analog, and the effects can be maintained for 2-3 hours. However, since Magnoliidae compounds easily pass the blood-brain barrier, they quickly and easily reach peak concentration in the brain tissue. Therefore, doses as low as 1 mg/Kg of body weight can cause nicotine-desensitization and decrease nicotine use.

Also because of the ease in passing the blood-brain barrier, administration of Magnoliidae compounds can be accomplished in several ways. It is important to note that administration of Magnoliidae compounds can occur either by administration of the Magnoliidae plant without purification or extraction of the Magnoliidae compounds, or by administration of the Magnoliidae compounds following extraction or purification. Therefore, administration of Magnoliidae described below includes both the extracted or purified Magnoliidae compounds, as well as the any part of a Magnoliidae plant.

Furthermore, administration of Magnoliidae can be in liquid form. Magnoliidae can be administered as a drink including, but not limited to, soft drinks, coffee, tea, nutritional and dietary supplement drinks, milk shakes, and protein shakes. Magnoliidae can also be administered sublingually in a chewing gum form. The method of administration with the Magnoliidae can also be by integrating it into sprays or lozenges to deliver sublingually to by-pass liver metabolism.

The method of administration with the Magnoliidae compounds can also be by making the Magnoliidae plant capable of respiratory inhalation. For example, parts of the Magnoliidae plant can be made into a tobacco-free cigarette or cigar. Administration in this manner is particularly desirable for reducing nicotine use while not requiring withdrawal from the psychological and behavioral aspects of smoking.

The method of administration with the Magnoliidae compounds can also be by making the Magnoliidae plant capable of respiratory inhalation. For example, parts of the Magnoliidae plant can be made into a tobacco-free cigarette or cigar. Administration in this manner is particularly desirable for reducing nicotine use while not requiring withdrawal from the psychological and behavioral aspects of smoking.

Administration of Magnoliidae compounds can also be effectively accomplished by preparing the Magnoliidae compounds in injectable forms to deliver parenterally to by-pass liver metabolism and for faster and stronger actions. Magnoliidae compounds can be dissolved in injection solution and be prepared either for use as a subcutaneous injection or for use as a direct venous injection or in an intravenous solution.

Finally, Magnoliidae compounds can be made into a patch so that the Magnoliidae compounds can be administered by dermal application of the patch to the skin. A Magnoliidae compound patch can also be prepared with a nicotine additive, or other nicotine-replacement-therapy, for increased efficacy.

Various embodiments of the invention are described above in the Drawings and Description of Various Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

What is claimed is:

1. A method of attenuating nicotine withdrawal by desensitizing nicotinic acetylcholine receptors comprising the step of administering an effective amount of tetrahydroberberine or analog thereof to a subject having or at risk of having nicotine withdrawal such that nicotinic acetylcholine receptors are desensitized, wherein the analog is selected from the group consisting of l-tetrahydropalmatine and l-stepholidine.

2. A method as recited in claim 1, wherein the effective amount of the tetrahydroberberine or analog thereof is greater than 1 mg/kg body weight of the subject.

3. A method as recited in claim 1, wherein the effective amount of the tetrahydroberberine or analog thereof is about 10 mg/kg to about 50 mg/kg body weight of the subject.

4. A method as recited in claim 1, wherein the tetrahydroberberine or analog thereof is administered via a method selected from the group consisting of oral, sublingual, subcutaneous, topical, inhalation and intravenous.

5. A method as recited in claim 1, wherein the tetrahydroberberine or analog thereof is administered in a food product.

6. A method as recited in claim 1, wherein the tetrahydroberberine or analog thereof is administered in a dermal patch.

7. A method of reducing sensitization to nicotine by attenuating nicotine-induced dopamine release by nicotinic acetylcholine receptors comprising the step of administering an effective amount of tetrahydroberberine or analog thereof to a subject having or at risk of having sensitization to nicotine such that nicotine-induced dopamine release is attenuated, wherein the analog is selected from the group consisting of l-tetrahydropalmatine and l-stepholidine.

8. A method as recited in claim 7, wherein the effective amount of the tetrahydroberberine or analog thereof is greater than 1 mg/kg body weight of the subject.

9. A method as recited in claim 7, wherein the effective amount of the tetrahydroberberine or analog thereof is about 10 mg/kg to about 50 mg/kg body weight of the subject.

10. A method as recited in claim 7, wherein the tetrahydroberberine or analog thereof is administered via a method selected from the group consisting of oral, sublingual, subcutaneous, topical, inhalation and intravenous.

11. A method as recited in claim 7, wherein the tetrahydroberberine or analog thereof is administered in a food product.

12. A method as recited in claim 7, wherein the tetrahydroberberine or analog thereof is administered in a dermal patch.

13. A method of attenuating nicotinic acetylcholine receptors in a subject in need thereof comprising the step of administering an effective amount of tetrahydroberberine or analog thereof and an effective amount of nicotine to the subject, wherein the analog of tetrahydroberberine is selected from the group consisting of l-tetrahydropalmatine and l-stepholidine; and wherein the effective amount of the tetrahydroberberine or analog thereof is greater than 1 mg/kg body weight of the subject.

14. A method as recited in claim 13, wherein the effective amount of the tetrahydroberberine or analog thereof is about 10 mg/kg to about 50 mg/kg body weight of the subject.

15. A method as recited in claim 13, wherein the tetrahydroberberine or analog thereof is administered via a method selected from the group consisting of oral, sublingual, subcutaneous, topical, inhalation and intravenous.

16. A method as recited in claim 13, wherein the tetrahydroberberine or analog thereof is administered in a food product.

17. A method as recited in claim 13, wherein the tetrahydroberberine or analog thereof is administered in a dermal patch.

18. A method as recited in claim 13, wherein the effective amount of nicotine is less than 500 nM.

19. A method as recited in claim 13, wherein the effective amount of nicotine is greater than 1.0 μM.

20. A method of attenuating nicotinic acetylcholine receptors in a subject in need thereof comprising the step of administering an effective amount of tetrahydroberberine or analog thereof and an effective amount of nicotine to the subject such that nicotinic acetylcholine receptors are desensitized, wherein the analog of tetrahydroberberine is selected from the group consisting of l-tetrahydropalmatine and l-stepholidine; wherein the effective amount of the tetrahydroberberine or analog thereof is greater than 1 mg/kg body weight of the subject; and wherein the effective amount of nicotine is greater than 1.0 µM.

21. A method as recited in claim 20, wherein the effective amount of the tetrahydroberberine or analog thereof is about 10 mg/kg to about 50 mg/kg body weight of the subject.

22. A method as recited in claim 20, wherein the tetrahydroberberine or analog thereof is administered via a method selected from the group consisting of oral, sublingual, subcutaneous, topical, inhalation and intravenous.

23. A method as recited in claim 20, wherein the tetrahydroberberine or analog thereof is administered in a food product.

24. A method as recited in claim 20, wherein the tetrahydroberberine or analog thereof is administered in a dermal patch.

25. A method of treatment of nicotine withdrawal symptoms in a subject in need thereof comprising the step of administering an effective amount of tetrahydroberberine or analog thereof and an effective amount of nicotine to the subject such that nicotinic acetylcholine receptors efficacy is enhanced, wherein the analog of tetrahydroberberine is selected from the group consisting of l-tetrahydropalmatine and l-stepholidine; wherein the effective amount of tetrahydroberberine or analog thereof is greater than 1 mg/kg body weight of the subject; and wherein the effective amount of nicotine is less than 500 nM.

26. A method as recited in claim 25, wherein the effective amount of the tetrahydroberberine or analog thereof is about 10 mg/kg to about 50 mg/kg body weight of the subject.

27. A method as recited in claim 25, wherein the tetrahydroberberine or analog thereof is administered via a method selected from the group consisting of oral, sublingual, subcutaneous, topical, inhalation and intravenous.

28. A method as recited in claim 25, wherein the tetrahydroberberine or analog thereof is administered in a food product.

29. A method as recited in claim 25, wherein the tetrahydroberberine or analog thereof is administered in a dermal patch.

* * * * *